(12) United States Patent
Schmidt et al.

(10) Patent No.: US 7,912,532 B2
(45) Date of Patent: Mar. 22, 2011

(54) METHOD AND INSTRUMENT FOR SURGICAL NAVIGATION

(75) Inventors: Martin Schmidt, Schwartau (DE); Jochen Koetke, Hamburg (DE); Peter Schalt, Moorrege (DE); Stefan Oelckers, Berlin (DE); Rolf-Rainer Grigat, Halstenbek (DE); Lars Eckert, Munich (DE); Thomas Hoell, Halle (DE)

(73) Assignee: Moeller-Wedel GmbH, Wedel (DE)

( * ) Notice: Subject to any disclaimer, the term of this patent is extended or adjusted under 35 U.S.C. 154(b) by 1403 days.

(21) Appl. No.: 10/516,297

(22) PCT Filed: Jun. 11, 2003

(86) PCT No.: PCT/EP03/06130
§ 371 (c)(1),
(2), (4) Date: Dec. 15, 2005

(87) PCT Pub. No.: WO03/105709
PCT Pub. Date: Dec. 24, 2003

(65) Prior Publication Data
US 2006/0122516 A1    Jun. 8, 2006

(30) Foreign Application Priority Data

Jun. 13, 2002 (DE) ............................... 102 26 361
Oct. 21, 2002 (DE) ............................... 102 49 025

(51) Int. Cl.
*A61B 5/05* (2006.01)
(52) U.S. Cl. ........................................ 600/424; 600/425

(58) Field of Classification Search .................. 600/407, 600/473, 424, 436, 476, 427, 130, 122; 359/372, 359/368; 606/130, 129, 10, 2, 14
See application file for complete search history.

(56) References Cited

U.S. PATENT DOCUMENTS

| 5,352,233 | A | | 10/1994 | Anis |
| 5,545,160 | A | | 8/1996 | O'Rourke |
| 5,630,431 | A | | 5/1997 | Taylor |
| 5,790,307 | A | * | 8/1998 | Mick et al. ..................... 359/382 |
| 5,792,147 | A | * | 8/1998 | Evans et al. ................... 606/130 |
| 5,795,294 | A | | 8/1998 | Luber et al. |

(Continued)

FOREIGN PATENT DOCUMENTS
WO    01/43654    6/2001

*Primary Examiner* — Eric F Winakur
*Assistant Examiner* — Lawrence N Laryea
(74) *Attorney, Agent, or Firm* — Oblon, Spivak, McClelland, Maier & Neustadt, L.L.P.

(57) ABSTRACT

The invention relates to a method for positional optimization in navigation, in particular neural navigation in surgery with an operation microscope and at least one optoelectronic image detector which may be connected to the microscope and also a computer system. The data obtained from the at least one image detector which lie in the microscope field-of-view for the operator, contain information on the position of an operation instrument, in particular the instrument tip. The actual position of the instrument in the x- and y-direction as well as in the z-direction of a three-dimensional coordinate system is continuously or intermittently determined from the relevant positional data. A separation determination is carried out for the positional determination in the z-direction by means of depth of focus evaluation and/or stereoscopic image analysis. The invention further relates to a navigation instrument, using marking, close to the instrument tip, lying within the field of view of the microscope during use thereof.

26 Claims, 3 Drawing Sheets

U.S. PATENT DOCUMENTS

| | | |
|---|---|---|
| 5,807,387 A | 9/1998 | Druais |
| 5,971,997 A * | 10/1999 | Guthrie et al. ............... 606/130 |
| 6,006,126 A | 12/1999 | Cosman |
| 6,036,637 A | 3/2000 | Kudo |
| 6,661,571 B1 * | 12/2003 | Shioda et al. ............... 359/372 |
| 2001/0055062 A1 * | 12/2001 | Shioda et al. ............... 348/79 |
| 2002/0002330 A1 | 1/2002 | Vilsmeier |
| 2002/0151784 A1 | 10/2002 | Mizoguchi et al. |
| 2004/0243147 A1 * | 12/2004 | Lipow ............... 606/130 |
| 2004/0254454 A1 * | 12/2004 | Kockro ............... 600/424 |

* cited by examiner

METHOD AND INSTRUMENT FOR SURGICAL NAVIGATION

The invention relates to a method for the optimization of identification of the current position in navigation, especially neuronavigation, in surgery with an operating microscope and at least one optoelectronic image receiver, which may also be connectable to the microscope, and a computer system according to the preamble of patent claim 1, and to a navigational instrument, especially for a method for the optimization of identification of the current position in navigation, especially neuronavigation.

Neuronavigation deals with the planning, but also with the performance of trajectories for surgical intervention at the human brain, the spine and the like. To this end, tomographies of the patient are made preoperatively, with markings provided on the patient's body which will likewise be detected by the tomography. Directly before the operation the three-dimensional location of said markers in space is determined by navigation, and a reference between the anatomy of the patient and the preoperatively recorded data records is thus produced. A corresponding process is called registration. Basically, a difference between optical navigation methods and magnetically working methods can be made. Both methods serve to determine the three-dimensional location and orientation of a special navigational pointer instrument in space, which serves to tap on relevant points. The location of the pointer tip in known optically working systems is not detected directly, but is determined with the aid of markers which, in most cases, are attached to the pointer in the form of balls. In the known systems reflectors for infrared light generated by special infrared light radiation sources are used as markers or marker substances. Two cameras located on a tie-bar then record the images and determine the location of the pointer in space.

According to methods based on magnetic fields the pointers comprise sensors which serve to detect the spatial location either from a generated magnetic alternating field or from a pulsed magnetic continuous field.

Optical systems have the disadvantage that there is the danger of the camera being covered by the operating staff. Magnetic systems fail to operate once objects made of soft iron are in the proximity thereof, which upset or distort the magnetic fields.

The basic object of the navigational systems available on the market resides in that—as was briefly outlined above—the position or the tip of an instrument, with which a detail in the field of operation is pointed to during the operation, is correlated with data from preoperative diagnostic methods, such as computerized tomography or magnetic resonance tomography. After such a correlation has taken place, for example, the position of a point in situs, to which the surgeon points with the aforementioned instrument during the operation, may be indicated to him in the images of the preoperative photographs in real-time. In this manner the surgeon obtains information with respect to the current position relative to a position of a structure recognizable in the CT- or MR-image, e.g. a tumor.

One possibility to represent this information to an operating surgeon is to register the position of the instrument tip in a previously selected CT- or MR-image as a point. For allowing the navigational system to fulfill this task, both the location and the orientation of the patient as well as those of the aforementioned surgical instrument must be known. As was explained, this information is, in current systems, detected for example by means of a pair of stereo cameras, which is located in the proximity of the operating table and detects the operating instrument.

Other known navigation systems moreover offer the possibility of overlapping images from preoperative diagnostic methods with the optical image of an operating microscope in the correct position, orientation and scale. In order to achieve this, the position and the orientation of the operating microscope as well as the currently selected magnification and plane of focus must additionally be detected. In the known navigational systems this detection of position and orientation of the operating microscope takes in most cases place by providing reflecting markings on the microscope which, just like the aforementioned markings on the pointer, are detected by said two cameras on the aforementioned tie-bar. Moreover, there is a known system according to which the relative position and orientation of the microscope is detected by means of angle of rotation transmitters in the microscope carrier system. The disadvantage in said last-mentioned systems resides in that the carrier systems used therefor required a reinforcement so as to ensure a sufficient exactness, which renders them disproportionately heavy and expensive. The overlapping itself may then, for example, be effected by reflecting the CT- or MR-image into the optical observation beam path of the microscope by means of a projector.

The navigational systems according to the prior art show some substantial disadvantages. This includes, inter alia, the fact that the markings on the surgical instrument or, respectively, on the pointer must at any time be visible to the pair of stereo cameras disposed on the camera arm. If the markings are covered, the functional capability is negatively influenced and errors in the data acquisition occur. According to experience the so-called position-identifying times of optical, but also of magnetic navigation systems are about ⅔. In addition, the large distance between the markings of the known optical instruments and the camera pair causes large measuring inaccuracies in the optical measurement, and relatively large-volume markings are required.

Another problem with current neurosurgical navigational systems resides in the motion of the brain tissue after the skullcap was opened and during the operation. This fact called brain shift results in that the geometry of the tissue during the operation no longer unlimitedly corresponds to the geometry of the tissue during the preoperative diagnostic method. This leads to errors, for example, in the aforementioned position indication of a pointer instrument relative to the tissue structures in a preoperative diagnostic MR- or CT-image. The error as described may be corrected, for example, by tracking the change of location of the tissue surface in the surroundings of the field of operation during the operation. To this end, the surgeon must, however, repeatedly tap on and mark several points on the aforementioned tissue surface with a marking instrument of the navigational system so as to make the data required for this correction available to the system. Given the stress, which in a neurosurgical operation is high enough anyhow, this constitutes a disadvantage, however.

By taking into account the aforementioned disadvantages of the prior art, the aim of navigational systems to be newly provided therefore resides in allowing a three-dimensional measurement of the field of operation and a tracking of the trajectories of the tip of the operating instrument, and in achieving an increased position identification, especially in the case of optical navigation. In addition, the large, expensive and occlusion-susceptible camera tie-bars are to be avoided. The handling of the systems is to be made simple and easy to survey so as to preclude error sources right from the beginning.

According to the above it is, therefore, the object of the invention to provide a method for optimizing the identification of the current position in navigation, especially neuronavigation, in surgery, which is based on an operating microscope known per se and at least one optoelectronic image receiver directly or indirectly coupled to the observation beam path of the microscope.

Moreover, a partial object of the invention resides in creating a novel navigational instrument, especially for use in operations by means of an operational microscope.

The object of the invention is provided by a method for optimizing the identification of the current position in navigation according to the definition of patent claim 1 and, in view of the navigational instrument, by the combination of features according to patent claim 12 and, in view of the operating microscope, by the teaching of claims 18 et seq.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 1:
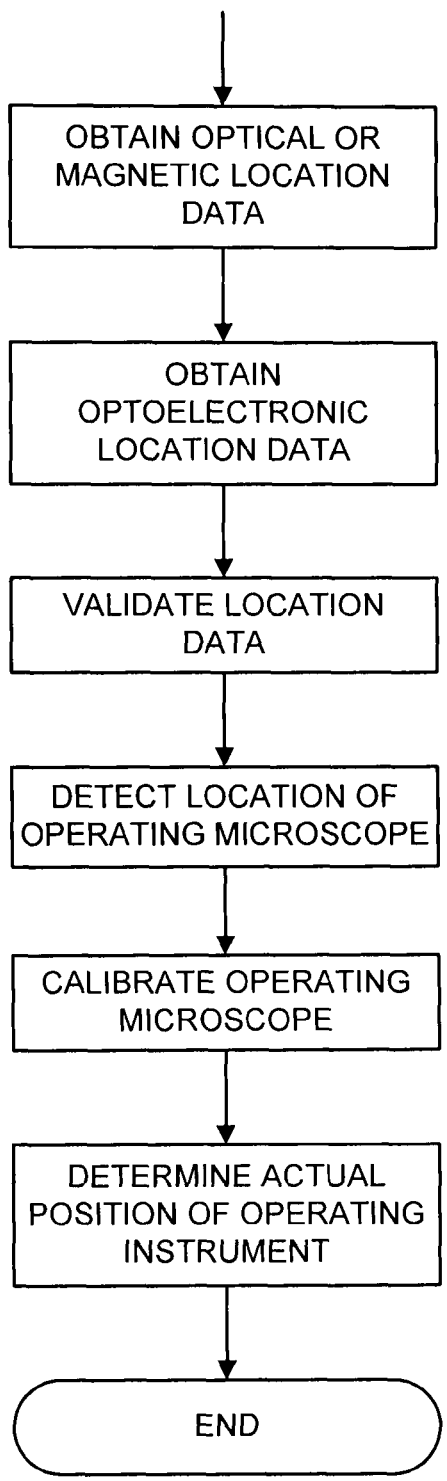
FIG. 1 is a flowchart depicting a process and algorithm in accordance with preferred aspects of this disclosure.
Figure 2:
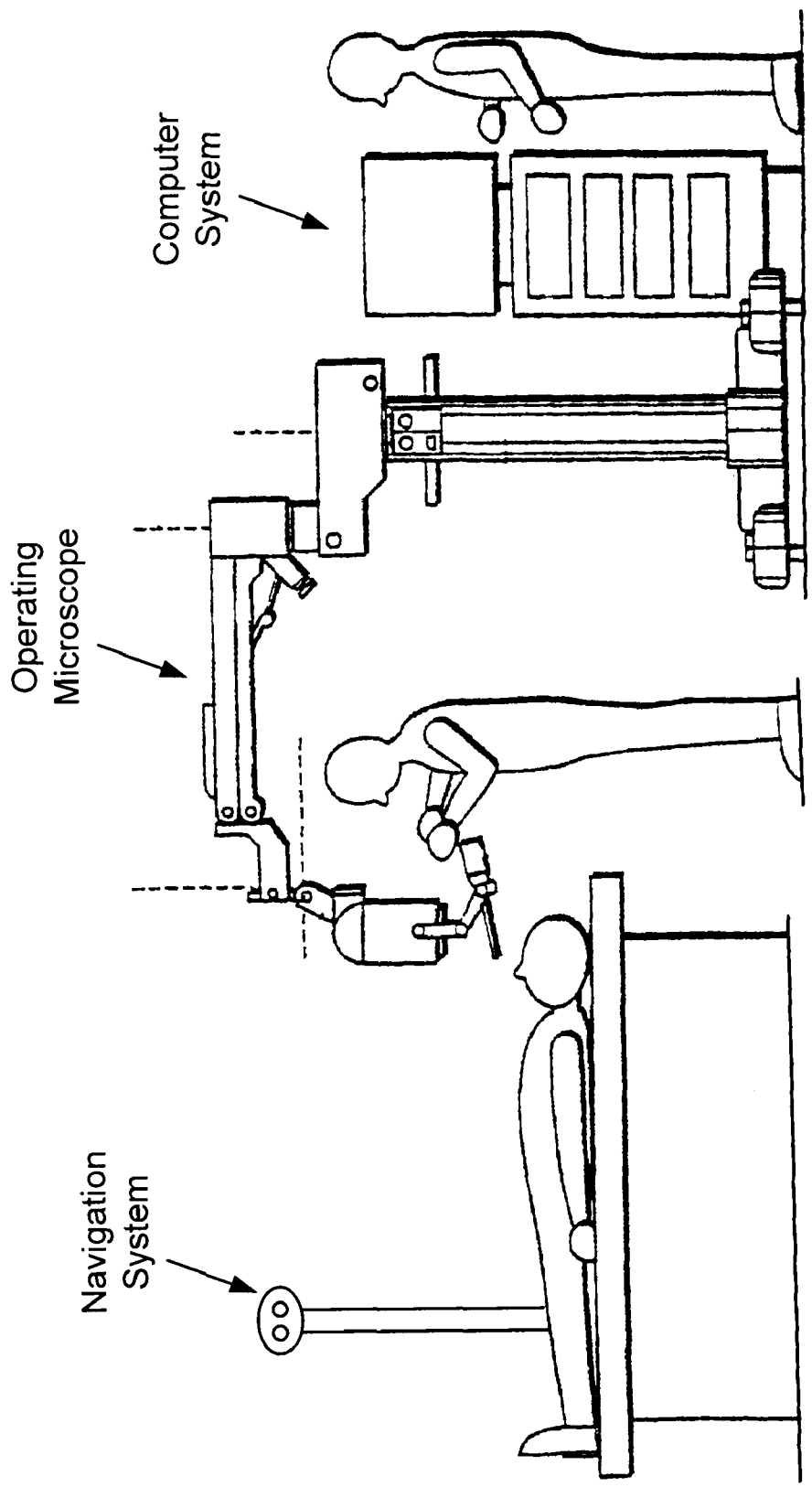
FIG. 2 is an illustrated view of a surgical suite including a patient, a surgeon, an assistant, an operating microscope and a computer system according to aspects of this disclosure.
Figure 3:
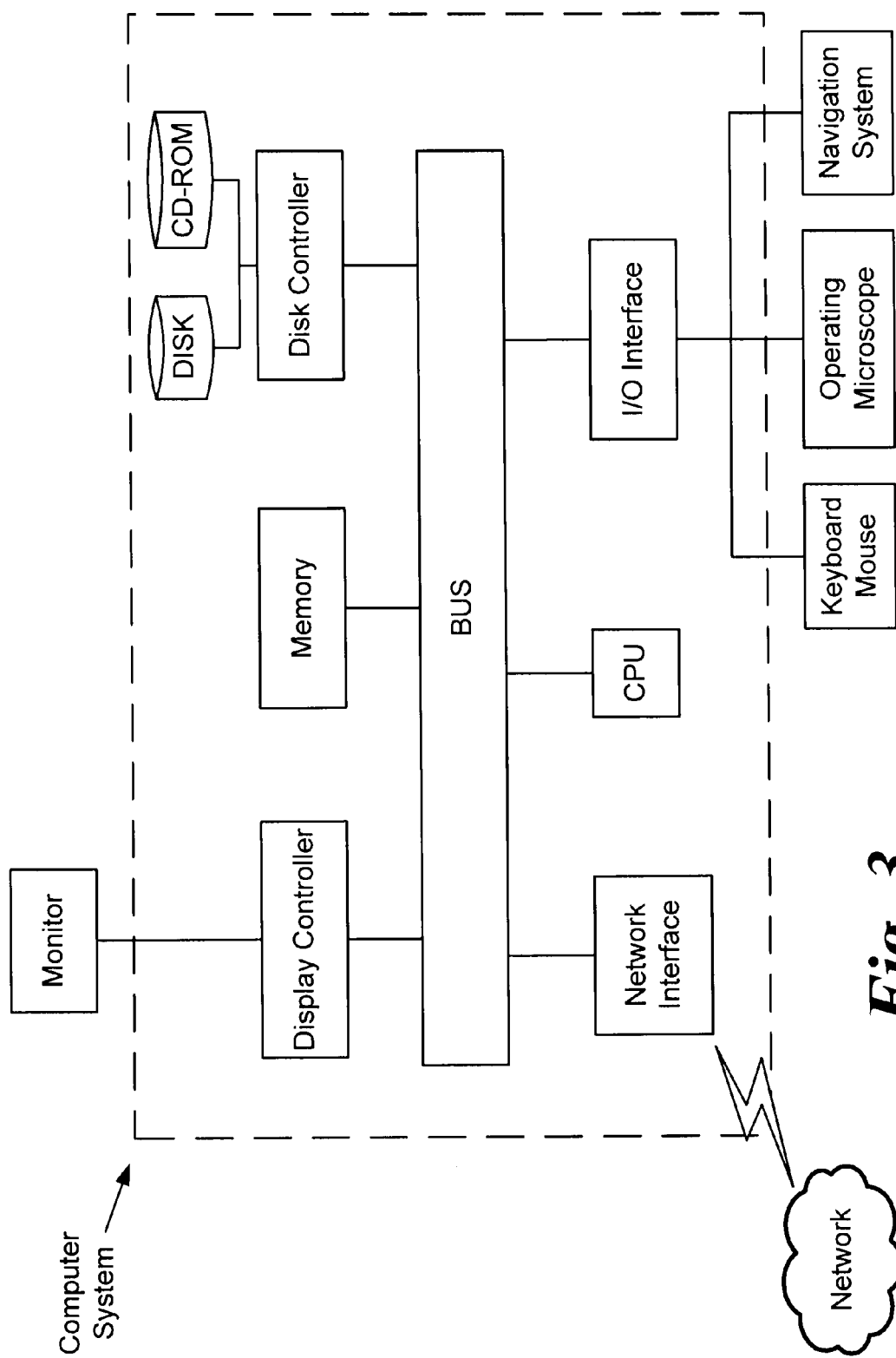
FIG. 3 is a schematic diagram of a computer system for processing the various algorithms and processes described in this disclosure.

Accordingly, the basic idea of the invention is to improve the position-identifying time of a navigational system by including the images from or parallel to the observation channels of the operating microscope in the actual image analysis of said system and to achieve additional advantageous effects, especially under the aspect of improving the exactness of the positional determination.

The data obtained from the at least one image receiver, each of which lie in the microscope field-of-view of the operator, contain information about the location of the operating instrument or pointer as used, especially of the tip thereof, wherein the actual position of the instrument in the x- and y-direction as well as in the z-direction of a three-dimensional coordinate system is continuously or intermittently determined from the relevant location data. For the positional determination in the z-direction either a distance determination is carried out by means of a depth of focus evaluation, or a stereoscopic image analysis is performed. Instead of two cameras with a stereoscopic image analysis also a novel optoelectronic image receiver designated as PMD array (PMD: Photonic Mixer Device) may be used. The measuring method of these sensors is related to the "time of flight" distance measuring method, but achieves, by novel principles with a smaller amount of apparatus and substantially smaller construction sizes, a better measuring exactness and may additionally be designed as a sensor array, with the result that it becomes feasible for the representation of an area to be topographed on a PMD array to obtain a complete topography with one measurement only. Since, due to the topography of a pointer, the pointer and the suitably formed markings thereof are easy to separate before the background of the field of operation, such a PMD array may also be used for tracking said pointer. If a PMD sensor is used, the object field of the sensor must be illuminated with an appropriately modulated and preferably narrow-banded light source, and the background light as well as the unmodulated white light of the operating microscope must be discriminated by suited filters prior to impinging the PMD array.

The optoelectronic image receiver(s) may directly be coupled to the observation beam path, especially by means of a beam splitter, wherein it also possible, however, to provide at least one separate image receiver beam path not being dependent on the observation beam path, which is likewise directed to the microscope field-of-view of the operator.

According to an embodiment the location of the operating microscope in space is detected, and said operating microscope positional data are supplied to a computer system known per se so as to transform the instrument positional data into a higher ranking space coordinate system by including existing data on the current position of the patient and preoperatively obtained three-dimensional data from the interior of the patient.

According to one embodiment of the invention it is possible, beside the data acquisition for the intraoperative location and position determination of a navigational instrument by means of known optical and/or magnetic methods, to carry out a supplementary three-dimensional position detection by means of the data provided by the image receiver of the operating microscope.

When using said two independent redundant systems, the hereinafter mentioned advantageous possibilities arise. If one of the systems does not supply any valid measured values, for example due to the covering of the markings, the measured values of the respective other system may be used, thereby allowing an increase of the position-identifying time. In case of redundant valid measured values the exactness of the measurement may be increased, for example, by averaging. In case of redundant valid measured values also the uncertainty of the measured values, e.g. due to the difference of the redundant measured values, may be quantified, whereby, for the first time, a navigational system is created which is more or less capable of performing a self-control. Even though the latter is standard for the major part of medical apparatus being critical for the safety of patients, it has so far not been realized in known navigational systems.

For detecting the location of the operating microscope in space a module is provided as an alternative to the known methods, which is integrated in the microscope or at least is connected with the microscope in a fixed and positionally invariant manner, which may do without the use of the space-filling tie-bars with cameras used in known systems and to be positioned next to the operating table. This module allows the microscope to detect its relative position in space or relative to the patient "by itself". The components and measuring methods mentioned in claims 19 to 24 are thereby applied individually or in a combination thereof. For minimizing the size of the aforementioned module, required infrastructure (power supply mechanisms, computers etc.) may be integrated, for example, in the base of the carrier system.

If the microscope "itself" is able to determine its position in space or, respectively, relative to the patient, and if also the tracking of the pointer is realized without the stereo camera pair of the conventional navigational system, the stereo camera pair of the conventional navigational system may be dropped. In this case, space in the operating theatre is considerably saved. Moreover, the initiation is facilitated since fewer devices with fewer cables have to moved and operated before the operation starts and, furthermore, the danger of occlusions during the operation is eliminated or at least considerably reduced.

With respect to the problems involved by the so-called brain shifting it is provided according to the invention to arrange marking points at or on the tissue surface of the patient, the change of location of which detected by the image receivers and determined by the computer system is used to carry out a correction of preoperatively obtained data in relation to the current state.

As is known, a stereoscopic light microscope may either consist of two convergent monocular mono-objective microscopes, or may comprise two optical channels brought out of center behind a common front lens. Due to construction-specific advantages operating microscopes are nearly exclusively structured as so-called common main objective (CMO) microscopes. The modeling of a CMO-microscope in an optical view is, however, extremely difficult as the treatment of so-called skew light beams becomes necessary. This is based on the lateral displacement of both optical channels behind the aforementioned common front lens.

If a stereoscopic analysis for neuronavigation becomes necessary, the person skilled in the art will at first preclude the use of CMO-microscopes by taking into account the aforementioned problems.

According to the invention this prejudice was overcome by finding an exclusively analytic formulation of the microscope model, which eventually corresponds to two rectified pin diaphragm cameras where corresponding points in both views theoretically lie on the corresponding image parts. By this finding the additional image processing steps may strongly be facilitated and image processing techniques known per se may be used.

Therefore, in accordance with the invention, the data obtained by the image receiver provided for each channel are corrected in view of the distortion errors in the x- and y-direction and in view of the disparity errors in the z-direction. This correction depends of the respective adjustments of the microscope, i.e. zoom and focus.

For the error correction a calibration is at first performed wherein, as was mentioned above, the operating microscope is described as a two-pin diaphragm camera on the image side. The calibration is carried out for all zoom and focus stages. The obtained calibration data are stored so as to allow an online or offline error correction at a later time. Of course, it is possible to store microscope-specific error correction data in a look-up table, so that the actual correction process can be facilitated under a calculation-technical aspect and thereby shortened.

All physical quantities required for calculating the nominal pin diaphragm camera parameters for a CMO-microscope are easily accessible and can typically be inferred from the manufacturer's data sheet. Initial values for an iterative calibration may be measured on the microscope in an easy manner. The required data concerning the image receivers, e.g. CCD sensors, are likewise available as manufacturer's data. The knowledge of internal lens data is not necessary. The CMO-microscope-adapted stereoscopic image processing is accomplished by a method in which the representation from both two-dimensional camera planes is formulated into the three-dimensional space by polynominal approximations of a smallest possible degree. A required control point quantity acts as supporting point quantity for the polynomials and is chosen in the entire volume.

For the practical application of microscopes with a continuously variable zoom and/or focus it is proposed to calibrate the individual system parameters in several zoom and focus settings and, when setting intermediate values, to interpolate the corresponding system parameters from the calibrated supporting points. The current settings of zoom and focus are to be made available to the analyzing unit during the calibration procedure, but also during the measuring procedure, advantageously by the microscope via a data line.

In connection with the novel navigational instrument according to the invention, especially for use in a method using image information from the beam path of a neuronavigational operating microscope, markings, especially micromarkings, are provided in the proximity of the instrument tip, namely basically when used lying in the field of view of the microscope. A certain minimum interspace to the instrument tip is due to the necessity that the markings are not to be contaminated by blood or other body liquids and, in case of convex markings, the use of the pointer instrument must not be obstructed.

The markings may, for example, be formed as at least three coplanar colored balls lying in one plane, which extends parallel to the longitudinal axis of the instrument, but does not include the same. Other embodiments are constituted by colored or reflecting annular markings. If the microscope is to be operated over a particularly large zoom and focus range, it may happen that the markings no longer completely lie in the field of view of the microscope if the magnifications are particularly strong and the lengths of focus too short, or that the markings are too small if the magnifications are particularly weak and the lengths of focus are large. In this case it is useful to attach several sets of markings having different sizes, wherein the smallest set of markings points or is attached closest to the instrument tip.

The navigational instrument according to the invention is sterilizable and can well be recognized through the microscope. Its one end is formed as a marked tip and may be employed as pointer. In the case where the tip is not directly visible for operative reasons, it can be detected via the aforementioned markings and the other information relating to the shape of the instrument.

The inventively obtained increased position identification in the case of optical systems is achieved by that the image recording is directly effected by the microscope, whereby it is ensured that the navigational instrument is not covered by the fingers or another operating set. The risk of covering by operating staff, as takes place with conventional optical navigational systems, is here precluded from the very beginning. Due to the ability to measure relative distances of points in the coordinate system of the microscope a further possibility consists in differential navigation, i.e. distances from points to a reference point can be measured.

In contrast to navigational instruments on the market so far the markings according to the invention are positioned close to the tip. Since a navigation is effected through the microscope, moreover, far smaller markings may be used. This, again, makes it possible to fabricate the navigational instrument itself smaller and more inexpensively and, above all, to use the same more flexibly and more ergonomically.

An exemplary navigational instrument is formed as a bayonet-type round steel of substantially 4 mm, tapered over a range of substantially 30 mm at the tip. The bayonet-like shape or cranking is useful under the aspect that it can be excluded that the instrument is covered by fingers or the like for the area detected by the camera.

According to one embodiment, the aforementioned coplanar balls are used as markers, which have, for example, a diameter of about 1.5 mm. For rendering the segmentation of the balls against the background as simple as possible, the same are lacquered in different colors. In view of the specific properties of the situs, blue, green and violet and/or brilliant yellow are preferably used. The use of infrared-reflecting balls is likewise possible.

Since, according to the invention, the work may be performed with the light source provided on the microscope's side, the embodiment with colored markings can do without special ball coatings which reflect infrared radiation, for example, according to a distinct directional characteristic.

A further development of the invention resides in that the marker configuration is not placed upon and attached to the navigational instrument, but merely consists of overprints. In case of the required detection of the rotation of the navigational instrument about its own axis an angle coding extending in an azimuthal direction is, for example, conceivable.

The detection of the balls in the camera views is preferably accomplished by applying colored image processing methods. In dependence on the intensiveness of a possibly existing color cast, the same is directly compensated with the image recording by a white balance. To this end, a scaling of the intensities of the red and blue channel of each image receiver or each camera, respectively, takes place.

The feature extraction or pattern recognition, respectively, of the markings in the form of coplanar colored balls is effected by the fact that a ball-shaped object is imaged in a differentiated manner. If the central point of the ball does not lie on the vertical of the camera plane, the contour of the ball is projected as an ellipse. The form therefore allows conclusions to the position of the individual balls.

If the instrument tip is not directly visible in the camera images, the three-dimensional position of the pointer tip is determined from the three-dimensional positions of the ball centers.

Of course, the navigational instrument may also be formed of a common operation set in order to not unnecessarily interrupt the operation for navigational purposes.

For calculating the three-dimensional coordinates of the tip position from the three-dimensional ball centers, the underlying geometry is calibrated. To this end, a local instrument coordinate system originating from a ball in the middle is defined, from which two axes extend through the other two balls and the third axis is orthogonal to the so spanned plane. In this affine coordinate system the location of the pointer tip has three definite coordinates, so that it may be reconstructed indirectly via the reconstruction of the axes of the local instrument coordinate system. The affine coordinates are independent of the intrinsic or extrinsic parameters of the camera arrangement and can be calibrated for a number of predefined tip and ball coordinates.

In the present specification, the terms position and location are substantially used as synonyms. It lies within the range of knowledge of the person skilled in the art that, for detecting the location of a three-dimensional body in space, six coordinates, e.g. emission point/center of gravity or the like are to be indicated in x-, y- and z-orientation and with the three so-called Eulerian angles. One exception is only constituted by the instrument tip, which only requires three coordinates as spatial point for defining the location.

The invention will hereinafter be explained in more detail by means of embodiments.

According to a first embodiment the field of operation lies inside the head of a patient, and an operating instrument is positioned with a corresponding marking in the field of view of the operating microscope.

The images of both observation channels are led via a beam splitter to two image receivers, e.g. CCD cameras. The camera images are then evaluated by a computer, and the position of the operating instrument is calculated in the coordinate system of the microscope from the stereoscopic image analysis and the device parameters, such as zoom and focus settings, which are additionally outputted by the microscope via a data connection.

At the same time, the location of the microscope and the patient is detected in the coordinate system of the stereo camera arm by a stereo camera pair with corresponding cameras, which is positioned in the proximity of the operating table, by means of stereoscopic image analysis and with the aid of the patient markings and the microscope markings. This allows the offsetting of the coordinate systems of the microscope and the patient and, for example, the position of the operating instrument may be indicated in coordinates of the patient.

Optionally, markings on the operating instrument may additionally be detected and evaluated by the camera pair, which results in a redundant measurement of the determination of the position of the operating instrument.

According to another embodiment, a generation of marking points, lines or a grating into the field of view of the microscope may be performed with visible light or with radiation in the near-infrared range. Said marking points, lines or gratings can then be recorded with a corresponding camera coupled to one of the observation channels. By evaluating the camera image, the location of the marking points can be detected in coordinates relative to the microscope.

Technically, the aforementioned teaching can be realized by that light is led via a diaphragm into the observation channel of the operating microscope and is imaged on one spot in the plane of focus of the microscope. This light spot is then detected by a camera, especially a CCD camera. With known coordinates in x- and y-direction of the diaphragm aperture in a Cartesian coordinate system perpendicular to the optical axis it then becomes possible, together with coordinates of the light spot on the camera chip, to work analogously to the common stereoscopic image analysis. Thus, the location of the spot, on which the light entering though the diaphragm is imaged, can be determined in coordinates of the microscope. As was mentioned above, light projection systems may be used instead of the illuminated diaphragm, each of which project a number of points, lines or gratings into the field of operation.

In case of a light grating, crossing points may be detected by the cameras. By means of the stereoscopic image analysis the coordinates of the crossing points of the light grating are then determinable on the surface of the field of operation in the coordinate system of the microscope. The information derived therefrom can then be represented as a three-dimensional perspective grating in the form of contour lines or the like on a display and may be used for the allocation of the location relative to preoperative recordings.

As part of quality assurance video recordings and photographs are, in most cases, made in today's operating theatres. Said video recordings and photographs do neither contain any quantitative three-dimensional information, nor can those generally be extracted from said video recordings and photographs.

If the recording of topographies of the field of operation during the operation is successful with an acceptable amount of work involved, the lack of the quantitative 3D-information of today's documentation would be inapplicable. Such topographies can be stored without problems and, within the framework of quality-assuring measures, for example, the actual resection profile can be compared with the findings from preoperative diagnostic data, such as the magnetic resonance tomography and the computerized tomography. Corresponding topographies may also be visualized to the doctor, for example, as relief diagrams, already during the operation.

Thus, it becomes possible—in addition to postoperative quality assurance —to offer decision aids for optimizing the resection boundaries to the surgeon already during the operation.

In principle, a topography of the object field of the microscope can already be obtained with the above-described microscope comprising stereo cameras by means of common stereoscopic image analysis methods. Especially the correspondence analysis is, however, very time-consuming and susceptible to errors for natural, possibly weakly structured fields.

An improvement can be achieved by the following description of the methods and devices, inter alia, for the projection of light markings.

By means of light markings the corresponding points required for the stereoscopic image analysis can be determined fast, precisely and with an extremely low error rate.

One possible first embodiment makes use of stereo cameras permanently connected to the microscope and a projection system which need not necessarily be permanently connected to the microscope.

A second embodiment is based on the light projection device at the location of one of both stereo cameras, with the use of the optical channels/paths which were used in the first mentioned embodiment by exactly this camera. In this case the methods of stereoscopic image analysis can already be applied with one camera only, which is known by the term inverse camera.

According to another embodiment the topography is obtained directly from the data of a PMD array (PMD: Photonic Mixer Device) and an associated personal computer.

According to the first embodiment a generation of marking points, lines or gratings into the field of view of the microscope may be performed with visible light or with radiation in the near-infrared range.

The tissue in the field of view of the operating microscope can then be recorded together with the marking points, lines or gratings projected onto said tissue by two cameras which are, for example, coupled to the observation channels of the microscope. By evaluating the camera images with the stereoscopic image analysis the location of the marking points can be detected in coordinates relative to the microscope. The principal error source of the stereoscopic image analysis—the correspondence analysis—is thereby drastically facilitated and error-proof, since only the marked points of both camera images are included in the evaluation, in connection with which the uncertainty of the correspondence allocation is essentially smaller than with unmarked points.

For obtaining a topography of the marked points in coordinates of the patent—instead of in coordinates of the microscope—the relative location and orientation of the patient and the microscope must be detected, which may be accomplished in the explained manner.

The procedure according to the second embodiment is largely analogous to the first embodiment. Instead of the two cameras coupled to the observation channel of the microscope, however, one of the cameras is replaced by a diaphragm. The same lens system, which had previously imaged the object field onto said camera, is now used to image the diaphragm onto the object field. If a diaphragm structured with points, lines or gratings is used, and light is led through said diaphragm structures and the associated optical channel onto the object field, and if the correspondingly illuminated area is recorded with the remaining camera, the principle of the inverse camera is applicable, and the methods of stereoscopic image analysis are usable despite the use of one camera only. With respect to the error security here, too, the advantages of the first embodiments apply. If invisible light is used, visible light may additionally be admixed so as to make the supporting points of the topography visible already in the image of the ocular of the microscope.

In a third embodiment a PMD sensor array is used instead of the conventional cameras. For being able to use the same, modulated light must be used for illumination in addition to the visible light of the microscope. The PMD sensor is protected against a too intensive illumination by the white non-modulated light by suited optical filters. The topography of the field imaged on the PMD sensor array may be obtained with this new technology directly from the PMD chip with an associated computer having a suited interface.

The topographical data obtained in the above embodiments can then, for example, as three-dimensional perspective grating or in the form of contour lines or the like, be represented on a display. Moreover, said topographical data can be represented location-correlated with data from preoperative diagnostic data (nuclear resonance scanning data, computerized tomography data etc.).

The invention claimed is:

1. A method for optimizing identification of a current position of an operating instrument in surgical navigation, including neuronavigation, with an operating microscope having an optoelectronic image receiver, the method comprising:
   obtaining first location data of a location of the operating instrument from an optical or magnetic navigation system;
   obtaining second location data of a location of the operating instrument from the optoelectronic image receiver of the operating microscope, said second location data further including data resulting from performing a depth of focus evaluation, a stereoscopic image analysis, or an evaluation of signals obtained by a PMD (Photonic Mixer Device) including the pertinent modulated illumination to supplement a depth component of the second location data; and
   determining an actual position of the operating instrument in a three-dimensional coordinate system based on the obtained first and second location data.

2. The method according claim 1, wherein
   when valid data records exist in only one of said first and second location data, the data determined as being valid are used for determining the position and location of the instrument or for tracking the instrument.

3. The method according to claim 1, wherein
   when redundant data records defined as being valid between said first and second location data exist, said first and second location data are used to increase measuring exactness or to quantify the measuring exactness.

4. The method according to claim 1, further comprising:
   detecting a location of the operating microscope in space with a stereo camera pair provided at or on the microscope, which allows a motion tracking relative to fixed markings provided to the patient or in space.

5. The method according to claim 1, further comprising:
   providing marking points at or on a tissue surface of a patient, a change of location of which is detected by the image receivers and determined by means of the computer system is used for determining a brain shifting at an open skull of the patient so as to perform a correction of preoperatively obtained data.

6. The method according to claim 1, wherein
   the operating microscope comprises two optical channels brought out of center behind a common front lens having a common object plane and a same magnification for both optical channels, wherein a correction function for distortion errors is incorporated in a stereoscopic image analysis, which is dependent on a currently used settings of zoom and focus.

7. The method according to claim 6, further comprising: calibrating for the correction of errors, wherein parameters of the correction function are empirically determined by calibration measurements at different settings of zoom and focus and different object interspaces and an obtained parameter set is stored.

8. An operating microscope for performing the method according to claim 1, wherein
the microscope comprises a module for detecting space coordinates relative to an operating room or to a patient.

9. An operating microscope according to claim 8, wherein the module includes a stereo camera pair with a computer for stereoscopic image analysis being associated therewith, wherein the stereo camera pair is aligned to marking points on the patient or in space, so that the location and orientation of the microscope relative to the patient or to the space can be determined.

10. An operating microscope according to claim 8, wherein the module includes a PMD sensor array with a computer for the evaluation of sensor data being associated therewith, wherein the PMD sensor array, with the pertinent optic and modulated illumination, is aligned to marking points on the patient or in space, so that the location and orientation of the microscope relative to the patient or to the space can be determined.

11. An operating microscope according to claim 8, wherein the module comprises a magnetic navigational system or components of such a system including echo sensors.

12. An operating microscope according to claim 8, wherein the module comprises one or more transmitters of a time of flight distance measurement system based on sound, ultrasound or on electromagnetic radiation, which operates in the time or frequency domain.

13. An operating microscope according to claim 8, wherein the module comprises one or more receivers of a time of flight distance measurement system based on sound or ultrasound or on electromagnetic radiation, which operates in the time or frequency domain.

14. An operating microscope according to claim 8, wherein the module comprises gyroscopes or inclination sensors.

15. An operating microscope according to claim 8, wherein the module comprises arrangements or facilities for combining different measurement methods.

16. An operating microscope for performing the method according to claim 1, wherein
the measured distance value of a PMD sensor from a predefined area of the image field of the microscope, including a center of the image, is transmitted to the navigational system.

17. An operating microscope for performing the method according to claim 1, wherein
the measured distance value of a PMD sensor from a predefined area of the image field of the microscope, including a center of the image, is provided and used as correcting variable for the focusing unit of the microscope.

18. An operating microscope for performing the method according to claim 1, wherein
a device for projection of light markings is provided, wherein areas of the field of operation marked with said light are subjected to a stereoscopic image analysis by means of two cameras connected to the microscope.

19. An operating microscope according to claim 18, wherein
currently obtained topographic data are transmitted to a navigational system and are used by a same as starting data for correction of a brain shift.

20. An operating microscope according to claim 18, wherein
the measured distance value from a predefined area of the field of view of the microscope, including a center of the image, is transmitted to a navigational system.

21. An operating microscope according to claim 18, wherein
the measured distance value from a predefined area of the field of view of the microscope, including the center of the image, is transmitted to the focusing unit of the microscope as correcting variable.

22. An operating microscope according to claim 18, wherein
one or more supporting points of detected topograms are marked onto said points by a projection of visible light.

23. An operating microscope according to claim 18, wherein
either the optical observation channels of the microscope are used for the cameras, the device for the projection of light markings or the PMD sensor, or additional optical channels are provided and used.

24. An operating microscope for performing the method according to claim 1, the operating microscope comprising:
a device for the projection of light markings connected to the microscope and wherein the areas of the field of operation marked with said light can be evaluated by means of a camera connected to the microscope and stereoscopic image analysis by using the principle of the inverse camera.

25. An operating microscope for performing the method according to claim 1, wherein
the microscope comprises a PMD sensor module connected therewith, on which an image of situs is represented, and wherein an associated modulated illumination device is provided.

26. A system for optimizing identification of a current position of an operating instrument in surgical navigation, including neuronavigation, the system comprising:
an operating microscope including an optoelectronic image receiver;
means for obtaining first location data of a location of the operating instrument from an optical or magnetic navigation system;
means for obtaining second location data of a location of the operating instrument from the optoelectronic image receiver of the operating microscope, said second location data further including data resulting from performing a depth of focus evaluation, a stereoscopic image analysis, or an evaluation of signals obtained by a PMD (Photonic Mixer Device) including the pertinent modulated illumination to supplement a depth component of the second location data; and
means for determining an actual position of the operating instrument in a three-dimensional coordinate system based on the obtained first and second location data.

* * * * *